(12) United States Patent
Mayall

(10) Patent No.: US 7,157,261 B2
(45) Date of Patent: Jan. 2, 2007

(54) RAT SECRETED EMBRYONIC ALKALINE PHOSPHATASE

(75) Inventor: Timothy P. Mayall, Encinitas, CA (US)

(73) Assignee: Canji, Inc., Palo Alto, CA (US)

( * ) Notice: Subject to any disclaimer, the term of this patent is extended or adjusted under 35 U.S.C. 154(b) by 24 days.

(21) Appl. No.: 10/968,202

(22) Filed: Oct. 18, 2004

(65) Prior Publication Data

US 2005/0112747 A1    May 26, 2005

Related U.S. Application Data

(60) Provisional application No. 60/515,053, filed on Oct. 27, 2003.

(51) Int. Cl.
- *C12N 9/14*   (2006.01)
- *C12N 15/00*   (2006.01)
- *C12N 5/00*   (2006.01)
- *C07H 21/04*   (2006.01)
- *C12P 21/06*   (2006.01)

(52) U.S. Cl. .................. 435/196; 536/23.2; 435/320.1; 435/325; 435/69.1; 435/195; 435/252.3; 435/353

(58) Field of Classification Search ................ 435/195, 435/320.1, 325, 69.1, 196, 252.3, 353; 536/23.2
See application file for complete search history.

(56) References Cited

U.S. PATENT DOCUMENTS

2003/0104422 A1    6/2003    Thuillier et al.

OTHER PUBLICATIONS

Berger, J., et al., "Secreted Placental alkaline phosphatase: a powerful new quantitative indicator of gene expression in eukaryotic cells," *Gene*, 1988, pp. 1-10, vol. 66.

Cullen, B., et al., "Secreted Placental Alkaline Phosphatase as a Eukaryotic Reporter Gene," *Methods in Enzymology*, 1992, pp. 362-368, vol. 216, Academic Press, Inc.

*Primary Examiner*—Rebecca E. Prouty
*Assistant Examiner*—Malgorzata A. Walicka
(74) *Attorney, Agent, or Firm*—Townsend and Townsend and Crew LLP

(57) ABSTRACT

Rat secreted embryonic alkaline phosphatase and methods for it use are provided.

42 Claims, 2 Drawing Sheets

Figure 2

Alignment of different species SEAP proteins

SEQUENCE LISTING

<160> NUMBER OF SEQ ID NOS: 4

<210> SEQ ID NO 1
<211> LENGTH: 1530
<212> TYPE: DNA
<213> ORGANISM: Artificial Sequence
<220> FEATURE:
<223> OTHER INFORMATION: Description of Artificial Sequence:cloned
      secreted form of rat embryonic alkaline phosphatase (rSEAP)
      reporter gene

<400> SEQUENCE: 1

| | | | | | |
|---|---|---|---|---|---|
| atggcaatgt | ggggagcctg | cttgctgctg | ctgggcctca | gcctacagat | gtccctgagc | 60 |
| ctcgtcccag | tggaggagga | gaacccagca | ttctggaacc | gaaaggcagc | cgaggccctg | 120 |
| gaggctgcca | agaagctgca | gcccattcag | acgtcagcca | acaacctcat | catcctcatg | 180 |
| ggggacggga | tgggggtgtc | cacagtaacg | gctacccgga | tactaaaggg | acagcagcaa | 240 |
| ggccatctgg | gacctgagac | gccactagcc | atggaccgct | tcccacacat | ggctctgtcc | 300 |
| aaaacataca | acacagacaa | gcaggtcccg | gacagcgcag | gcacaggcac | ggcctttctc | 360 |
| tgcgggtca | aaccaatat | gaaggtcatt | ggcttgagtg | cagctgcacg | ctttaatcag | 420 |
| tgcaacacaa | cgtggggtaa | tgaggtcgtc | tcggtaatgc | accgtgctaa | gaaagcaggg | 480 |
| aagtctgtgg | gagtggtgac | caccacatcg | gtgcagcatg | cctctccagc | cggcacctac | 540 |
| gcacacactg | tgaaccgtaa | ctggtactcc | gatgcacaca | tgtccactgc | tgcactacag | 600 |
| gagggctgca | aggacatcgc | catgcagctc | atctccaaca | ccgacattga | tgtgatcctc | 660 |
| ggtggtggcc | gcaagttcat | gtttcctaag | ggaacaccag | accaggaata | tccgactgac | 720 |
| cctcagcaag | ctggaaccag | gctggatgga | cgcaatctag | ttcaggagtg | gctggcaaaa | 780 |
| caccagggtg | cccggtatgt | ttggaaccgc | acagagctca | tccaggcctc | cctgaacaga | 840 |
| tctgtgacac | acctcatggg | cctctttgaa | cctaatgaca | tgaaatacaa | catcgaccga | 900 |
| gaccctactc | aggatccctc | cctggccgag | atgacagagg | tggccgtgca | catgctcagc | 960 |
| aggaacccca | aaggcttcta | tctctttgtg | gaagggggcc | gcatcgacca | tggtcaccat | 1020 |
| gaagctatag | cctatcgtgc | actgactgag | gctgtcatgt | tcgactcagc | tgttgacaag | 1080 |
| gcagataagc | tcaccagtga | gaaggacacg | atgatcattg | tcaccgccga | ccactctcat | 1140 |
| gttttctctt | ttggtggtta | cacacagaga | gaggcctcca | ttttttgggct | ggctcccttc | 1200 |
| aaggctgggg | atggcaaatc | ctttacctcg | attctatacg | gcaatggtcc | tggctacaag | 1260 |
| ctcaacaatg | gcatccgggc | tgatgtcacc | gaggaagaga | gcagcaaccc | cacgtaccag | 1320 |
| cagcaggcgg | ctgtaccct | gtcgtcagag | acccacagtg | gggaggacgt | ggccatattt | 1380 |
| gcgcgtggcc | ctcaggcgca | cctggtgcac | ggagtgcagg | aacagaacta | catcgctcac | 1440 |
| gtcatggcct | tcgcaggctg | cctggagccc | tacaccgact | gcggccttgc | gccccctgct | 1500 |
| ggtcggagca | gtgcagtgag | tccaggctga | | | | 1530 |

<210> SEQ ID NO 2
<211> LENGTH: 509
<212> TYPE: PRT
<213> ORGANISM: Artificial Sequence
<220> FEATURE:
<223> OTHER INFORMATION: Description of Artificial Sequence:cloned
      secreted form of rat embryonic alkaline phosphatase (rSEAP)
      reporter polypeptide

<400> SEQUENCE: 2

```
Met Ala Met Trp Gly Ala Cys Leu Leu Leu Gly Leu Ser Leu Gln
  1               5                  10                  15

Met Ser Leu Ser Leu Val Pro Val Glu Glu Asn Pro Ala Phe Trp
             20                  25                  30

Asn Arg Lys Ala Ala Glu Ala Leu Glu Ala Ala Lys Lys Leu Gln Pro
         35                  40                  45

Ile Gln Thr Ser Ala Asn Asn Leu Ile Ile Leu Met Gly Asp Gly Met
     50                  55                  60

Gly Val Ser Thr Val Thr Ala Thr Arg Ile Leu Lys Gly Gln Gln Gln
 65              70                  75                      80

Gly His Leu Gly Pro Glu Thr Pro Leu Ala Met Asp Arg Phe Pro His
                 85                  90                  95

Met Ala Leu Ser Lys Thr Tyr Asn Thr Asp Lys Gln Val Pro Asp Ser
            100                 105                 110

Ala Gly Thr Gly Thr Ala Phe Leu Cys Gly Val Lys Thr Asn Met Lys
            115                 120                 125

Val Ile Gly Leu Ser Ala Ala Ala Arg Phe Asn Gln Cys Asn Thr Thr
130                 135                 140

Trp Gly Asn Glu Val Val Ser Val Met His Arg Ala Lys Lys Ala Gly
145                 150                 155                 160

Lys Ser Val Gly Val Val Thr Thr Thr Ser Val Gln His Ala Ser Pro
                165                 170                 175

Ala Gly Thr Tyr Ala His Thr Val Asn Arg Asn Trp Tyr Ser Asp Ala
            180                 185                 190

His Met Ser Thr Ala Ala Leu Gln Glu Gly Cys Lys Asp Ile Ala Met
        195                 200                 205

Gln Leu Ile Ser Asn Thr Asp Ile Asp Val Ile Leu Gly Gly Gly Arg
    210                 215                 220

Lys Phe Met Phe Pro Lys Gly Thr Pro Asp Gln Glu Tyr Pro Thr Asp
225                 230                 235                 240

Pro Gln Gln Ala Gly Thr Arg Leu Asp Gly Arg Asn Leu Val Gln Glu
                245                 250                 255

Trp Leu Ala Lys His Gln Gly Ala Arg Tyr Val Trp Asn Arg Thr Glu
            260                 265                 270

Leu Ile Gln Ala Ser Leu Asn Arg Ser Val Thr His Leu Met Gly Leu
        275                 280                 285

Phe Glu Pro Asn Asp Met Lys Tyr Asn Ile Asp Arg Asp Pro Thr Gln
    290                 295                 300

Asp Pro Ser Leu Ala Glu Met Thr Glu Val Ala Val His Met Leu Ser
305                 310                 315                 320

Arg Asn Pro Lys Gly Phe Tyr Leu Phe Val Glu Gly Gly Arg Ile Asp
                325                 330                 335

His Gly His His Glu Ala Ile Ala Tyr Arg Ala Leu Thr Glu Ala Val
            340                 345                 350

Met Phe Asp Ser Ala Val Asp Lys Ala Asp Lys Leu Thr Ser Glu Lys
        355                 360                 365

Asp Thr Met Ile Ile Val Thr Ala Asp His Ser His Val Phe Ser Phe
370                 375                 380

Gly Gly Tyr Thr Gln Arg Glu Ala Ser Ile Phe Gly Leu Ala Pro Phe
385                 390                 395                 400

Lys Ala Gly Asp Gly Lys Ser Phe Thr Ser Ile Leu Tyr Gly Asn Gly
                405                 410                 415
```

-continued

```
Pro Gly Tyr Lys Leu Asn Asn Gly Ile Arg Ala Asp Val Thr Glu Glu
            420                 425                 430

Glu Ser Ser Asn Pro Thr Tyr Gln Gln Gln Ala Ala Val Pro Leu Ser
        435                 440                 445

Ser Glu Thr His Ser Gly Glu Asp Val Ala Ile Phe Ala Arg Gly Pro
    450                 455                 460

Gln Ala His Leu Val His Gly Val Gln Glu Gln Asn Tyr Ile Ala His
465                 470                 475                 480

Val Met Ala Phe Ala Gly Cys Leu Glu Pro Tyr Thr Asp Cys Gly Leu
                485                 490                 495

Ala Pro Pro Ala Gly Arg Ser Ser Ala Val Ser Pro Gly
            500                 505
```

<210> SEQ ID NO 3
<211> LENGTH: 506
<212> TYPE: PRT
<213> ORGANISM: Artificial Sequence
<220> FEATURE:
<223> OTHER INFORMATION: Description of Artificial Sequence:translation
    of human secreted form of embryonic alkaline phosphatase (SEAP)
    reporter gene derived from native human placental alkaline
    phosphatase (hPLAP)

<400> SEQUENCE: 3

```
Met Leu Leu Leu Leu Leu Leu Gly Leu Arg Leu Gln Leu Ser Leu
 1               5                  10                  15

Gly Ile Ile Pro Val Glu Glu Asn Pro Asp Phe Trp Asn Arg Glu
            20                  25                  30

Ala Ala Glu Ala Leu Gly Ala Ala Lys Lys Leu Gln Pro Ala Gln Thr
        35                  40                  45

Ala Ala Lys Asn Leu Ile Ile Phe Leu Gly Asp Gly Met Gly Val Ser
    50                  55                  60

Thr Val Thr Ala Ala Arg Ile Leu Lys Gly Gln Lys Lys Asp Lys Leu
65                  70                  75                  80

Gly Pro Glu Ile Pro Leu Ala Met Asp Arg Phe Pro Tyr Val Ala Leu
                85                  90                  95

Ser Lys Thr Tyr Asn Val Asp Lys His Val Pro Asp Ser Gly Ala Thr
            100                 105                 110

Ala Thr Ala Tyr Leu Cys Gly Val Lys Gly Asn Phe Gln Thr Ile Gly
        115                 120                 125

Leu Ser Ala Ala Ala Arg Phe Asn Gln Cys Asn Thr Thr Arg Gly Asn
    130                 135                 140

Glu Val Ile Ser Val Met Asn Arg Ala Lys Lys Ala Gly Lys Ser Val
145                 150                 155                 160

Gly Val Val Thr Thr Thr Arg Val Gln His Ala Ser Pro Ala Gly Thr
                165                 170                 175

Tyr Ala His Thr Val Asn Arg Asn Trp Tyr Ser Asp Ala Asp Val Pro
            180                 185                 190

Ala Ser Ala Arg Gln Glu Gly Cys Gln Asp Ile Ala Thr Gln Leu Ile
        195                 200                 205

Ser Asn Met Asp Ile Asp Val Ile Leu Gly Gly Gly Arg Lys Tyr Met
    210                 215                 220

Phe Pro Met Gly Thr Pro Asp Pro Glu Tyr Pro Asp Asp Tyr Ser Gln
225                 230                 235                 240

Gly Gly Thr Arg Leu Asp Gly Lys Asn Leu Val Gln Glu Trp Leu Ala
                245                 250                 255
```

```
Lys Arg Gln Gly Ala Arg Tyr Val Trp Asn Arg Thr Glu Leu Met Gln
            260                 265                 270

Ala Ser Leu Asp Pro Ser Val Thr His Leu Met Gly Leu Phe Glu Pro
        275                 280                 285

Gly Asp Met Lys Tyr Glu Ile His Arg Asp Ser Thr Leu Asp Pro Ser
    290                 295                 300

Leu Met Glu Met Thr Glu Ala Ala Leu Arg Leu Leu Ser Arg Asn Pro
305                 310                 315                 320

Arg Gly Phe Phe Leu Phe Val Glu Gly Gly Arg Ile Asp His Gly His
                325                 330                 335

His Glu Ser Arg Ala Tyr Arg Ala Leu Thr Glu Thr Ile Met Phe Asp
            340                 345                 350

Asp Ala Ile Glu Arg Ala Gly Gln Leu Thr Ser Glu Glu Asp Thr Leu
        355                 360                 365

Ser Leu Val Thr Ala Asp His Ser His Val Phe Ser Phe Gly Gly Tyr
    370                 375                 380

Pro Leu Arg Gly Ser Ser Ile Phe Gly Leu Ala Pro Gly Lys Ala Arg
385                 390                 395                 400

Asp Arg Lys Ala Tyr Thr Val Leu Leu Tyr Gly Asn Gly Pro Gly Tyr
                405                 410                 415

Val Leu Lys Asp Gly Ala Arg Pro Asp Val Thr Glu Ser Glu Ser Gly
            420                 425                 430

Ser Pro Glu Tyr Arg Gln Gln Ser Ala Val Pro Leu Asp Glu Glu Thr
        435                 440                 445

His Ala Gly Glu Asp Val Ala Val Phe Ala Arg Gly Pro Gln Ala His
    450                 455                 460

Leu Val His Gly Val Gln Glu Gln Thr Phe Ile Ala His Val Met Ala
465                 470                 475                 480

Phe Ala Ala Cys Leu Glu Pro Tyr Thr Ala Cys Asp Leu Ala Pro Pro
                485                 490                 495

Ala Gly Thr Thr Asp Ala Ala His Pro Gly
            500                 505

<210> SEQ ID NO 4
<211> LENGTH: 507
<212> TYPE: PRT
<213> ORGANISM: Artificial Sequence
<220> FEATURE:
<223> OTHER INFORMATION: Description of Artificial Sequence:translation
      of mouse secreted form of embryonic alkaline phosphatase (mSEAP)
      reporter gene

<400> SEQUENCE: 4

Met Trp Gly Ala Cys Leu Leu Leu Gly Leu Ser Leu Gln Val Cys
1               5                   10                  15

Pro Ser Val Ile Pro Val Glu Glu Asn Pro Ala Phe Trp Asn Arg
                20                  25                  30

Lys Ala Ala Glu Ala Leu Asp Ala Ala Lys Lys Leu Lys Pro Ile Gln
            35                  40                  45

Thr Ser Ala Lys Asn Leu Val Ile Leu Met Gly Asp Gly Met Gly Val
        50                  55                  60

Ser Thr Val Thr Ala Thr Arg Ile Leu Lys Gly Gln Gln Gly His
65                  70                  75                  80

Leu Gly Pro Glu Thr Gln Leu Ala Met Asp Arg Phe Pro His Met Ala
                85                  90                  95

Leu Ser Lys Thr Tyr Asn Thr Asp Lys Gln Ile Pro Asp Ser Ala Gly
```

-continued

```
                100                 105                 110
Thr Gly Thr Ala Phe Leu Cys Gly Val Lys Thr Asn Met Lys Val Ile
        115                 120                 125
Gly Leu Ser Ala Ala Arg Phe Asn Gln Cys Asn Thr Thr Trp Gly
    130                 135                 140
Asn Glu Val Val Ser Val Met His Arg Ala Lys Lys Ala Gly Lys Ser
145                 150                 155                 160
Val Gly Val Val Thr Thr Ser Val Gln His Ala Ser Pro Ala Gly
                165                 170                 175
Thr Tyr Ala His Thr Val Asn Arg Gly Trp Tyr Ser Asp Ala Gln Met
            180                 185                 190
Pro Ala Ser Ala Leu Gln Asp Gly Cys Lys Asp Ile Ser Thr Gln Leu
        195                 200                 205
Ile Ser Asn Met Asp Ile Asp Val Ile Leu Gly Gly Arg Lys Phe
    210                 215                 220
Met Phe Pro Lys Gly Thr Pro Asp Gln Glu Tyr Pro Thr Asp Thr Lys
225                 230                 235                 240
Gln Ala Gly Thr Arg Leu Asp Gly Arg Asn Leu Val Gln Glu Trp Leu
                245                 250                 255
Ala Lys His Gln Gly Ala Arg Tyr Val Trp Asn Arg Ser Glu Leu Ile
            260                 265                 270
Gln Ala Ser Leu Asn Arg Ser Val Thr His Leu Met Gly Leu Phe Glu
        275                 280                 285
Pro Asn Asp Met Lys Tyr Glu Ile His Arg Asp Pro Ala Gln Asp Pro
    290                 295                 300
Ser Leu Ala Glu Met Thr Glu Val Ala Val Arg Met Leu Ser Arg Asn
305                 310                 315                 320
Pro Lys Gly Phe Tyr Leu Phe Val Glu Gly Gly Arg Ile Asp His Gly
                325                 330                 335
His His Glu Thr Val Ala Tyr Arg Ala Leu Thr Glu Ala Val Met Phe
            340                 345                 350
Asp Ser Ala Val Asp Lys Ala Asp Lys Leu Thr Ser Glu Gln Asp Thr
        355                 360                 365
Met Ile Leu Val Thr Ala Asp His Ser His Val Phe Ser Phe Gly Gly
    370                 375                 380
Tyr Thr Gln Arg Gly Ala Ser Ile Phe Gly Leu Ala Pro Phe Lys Ala
385                 390                 395                 400
Glu Asp Gly Lys Ser Phe Thr Ser Ile Leu Tyr Gly Asn Gly Pro Gly
                405                 410                 415
Tyr Lys Leu His Asn Gly Ala Arg Ala Asp Val Thr Glu Glu Ser
            420                 425                 430
Ser Asn Pro Thr Tyr Gln Gln Gln Ala Ala Val Pro Leu Ser Ser Glu
        435                 440                 445
Thr His Ser Gly Glu Asp Val Ala Ile Phe Ala Arg Gly Pro Gln Ala
    450                 455                 460
His Leu Val His Gly Val Gln Glu Gln Asn Tyr Ile Ala His Val Met
465                 470                 475                 480
Ala Phe Ala Ala Cys Leu Glu Pro Tyr Thr Asp Cys Gly Leu Ala Ser
                485                 490                 495
Pro Ala Gly Gln Ser Ser Ala Val Ser Pro Gly
            500                 505
```

RAT SECRETED EMBRYONIC ALKALINE PHOSPHATASE

CROSS-REFERENCE TO RELATED APPLICATIONS

The present application claims benefit of priority to U.S. Provisional Patent Application No. 60/515,053, filed on Oct. 27, 2003, which is incorporated by reference in its entirety for any purpose.

BACKGROUND OF THE INVENTION

Reporter genes have been used to analyze the expression of transgenes from various vectors. Reporter genes that have been used in animal models encode exogenous cytoplasmic or secreted proteins, such as bacterial β-galactosidase, insect luciferase, human growth hormone, human erythropoietin, and human and mouse-secreted alkaline phosphatase (SEAP). These reporter genes often are used for transient expression studies or tissue-specific expression studies. However, the proteins they encode are typically immunogenic. They can also elicit a cytotoxic T-lymphocyte response or a neutralizing antibody response that suppresses detection, leading to inaccurate reporter gene expression data (see Tripathy et al., *Nature Medicine* 2:545–50 (1996); and Yang et al., *Gene Therapy* 3:137–44 (1996)).

One reporter gene, the SEAP gene noted above, is derived from the native human placental alkaline phosphatase (hPLAP) (see, Cullen, B. R., and Malim, M. H. *Methods Enzymol* 216:362–8 (1992)) or mouse embryonic alkaline phosphatase (mSEAP) (see, e.g., U.S. Patent Application Publication 2003/0104422). The amino acid sequence typically used for its reporter gene function differs from the native gene by a deletion of C-terminal residues, which converts the membrane-bound protein into a secreted protein (Berger, et al., *Gene* 66, 1–10 (1988)).

The art however, has not described a rat SEAP gene. The rat sequence has particular use in studying long term expression in rat because, unlike proteins from other species, it does not induce an immune response. The present application addresses this and other problems.

BRIEF SUMMARY OF THE INVENTION

The present invention provides isolated polynucleotides encoding a polypeptide at least 95% identical to SEQ ID NO:2, wherein the polypeptide has alkaline phosphatase activity. In some embodiments, the polypeptide comprises a methionine (M) corresponding to the first amino acid of SEQ ID NO:2; an alanine (A) corresponding to the second amino acid of SEQ ID NO:2; and/or an arginine (R) corresponding to the 265th amino acid of SEQ ID NO:2.

In some embodiments, the polypeptide is depicted in SEQ ID NO:2. In some embodiments, the polynucleotide comprises SEQ ID NO:1.

The present invention also provides expression cassette comprising a promoter operably linked to a polynucleotide encoding a polypeptide at least 95% identical to SEQ ID NO:2, wherein the polypeptide has alkaline phosphatase activity. In some embodiments, the promoter is constitutive. In some embodiments, the promoter is inducible. In some embodiments, the promoter is tissue-specific.

The present invention also provides vectors comprising a promoter operably-linked to a polynucleotide encoding a polypeptide at least 95% identical to SEQ ID NO:2, wherein the polypeptide has alkaline phosphatase activity. In some embodiments, the polypeptide comprises a methionine (M) corresponding to the first amino acid of SEQ ID NO:2; an alanine (A) corresponding to the second amino acid of SEQ ID NO:2; and/or an arginine (R) corresponding to the 265th amino acid of SEQ ID NO:2.

In some embodiments, the polypeptide comprises SEQ ID NO:2. In some embodiments, the polynucleotide comprises SEQ ID NO:1.

In some embodiments, the vector is a viral vector. In some embodiments, the vector is an adenoviral vector. In some embodiments, the vector comprises a second expression cassette encoding a second polypeptide. In some embodiments, the vector is a plasmid.

The present invention also provides cells comprising a heterologous expression cassette, wherein the expression cassette comprises a promoter operably linked to a polynucleotide encoding a a polypeptide at least 95% identical to SEQ ID NO:2, and wherein the polypeptide has alkaline phosphatase activity. In some embodiments, the polypeptide comprises a methionine (M) corresponding to the first amino acid of SEQ ID NO:2; an alanine (A) corresponding to the second amino acid of SEQ ID NO:2; and/or an arginine (R) corresponding to the 265th amino acid of SEQ ID NO:2.

In some embodiments, the polypeptide comprises SEQ ID NO:2. In some embodiments, the polynucleotide comprises SEQ ID NO:1. In some embodiments, the expression cassette is integrated into the chromosomal DNA of the cell. In some embodiments, the expression cassette is part of a vector. In some embodiments, the vector is a viral vector. In some embodiments, the vector is an adenoviral vector.

In some embodiments, the cell is a mammalian cell. In some embodiments, the cell is a rat cell. In some embodiments, the cell is a prokaryotic cell.

The present invention also provides methods of expressing secreted embryonic alkaline phosphatase in a cell. In some embodiments, the methods comprise introducing a nucleic acid comprising an expression cassette comprised of a promoter operably linked to a polynucleotide encoding a polypeptide at least 95% identical to SEQ ID NO:2, wherein the polypeptide has alkaline phosphatase activity, thereby expressing secreted embryonic alkaline phosphatase in the cell.

In some embodiments, the polypeptide comprises a methionine (M) corresponding to the first amino acid of SEQ ID NO:2; an alanine (A) corresponding to the second amino acid of SEQ ID NO:2; and/or an arginine (R) corresponding to the 265th amino acid of SEQ ID NO:2. In some embodiments, the polypeptide comprises SEQ ID NO:2. In some embodiments, the polynucleotide comprises SEQ ID NO:1.

In some embodiments, the nucleic acid is a viral vector. In some embodiments, the viral vector is an adenoviral vector. In some embodiments, the viral vector comprises a second expression cassette encoding a second polypeptide.

In some embodiments, the cell is in an animal and the introducing step comprises administering the nucleic acid to the animal.

In some embodiments, the methods further comprise detecting expression of the polypeptide.

In some embodiments, the cell is in an animal; the introducing step comprises administering the nucleic acid to the animal; and the expression is detected at least 30 days after the nucleic acid was introduced into the cell.

In some embodiments, the animal is a rat.

The present invention also provides a rat infected with a recombinant adenovirus comprising a promoter operably-linked to a polynucleotide encoding a polypeptide at least 95% identical to SEQ ID NO:2, wherein the polypeptide has alkaline phosphatase activity. In some embodiments, the polypeptide comprises a methionine (M) corresponding to the first amino acid of SEQ ID NO:2; an alanine (A) corresponding to the second amino acid of SEQ ID NO:2; and/or an arginine (R) corresponding to the 265th amino acid of SEQ ID NO:2. In some embodiments, the polypeptide comprises SEQ ID NO:2. In some embodiments, the polynucleotide comprises SEQ ID NO:1.

The present invention also provides transgenic rats comprising a heterologous expression cassette, wherein the expression cassette comprises a promoter operably linked to a polynucleotide encoding a polypeptide at least 95% identical to SEQ ID NO:2, wherein the polypeptide has alkaline phosphatase activity. In some embodiments, the polypeptide comprises a methionine (M) corresponding to the first amino acid of SEQ ID NO:2; an alanine (A) corresponding to the second amino acid of SEQ ID NO:2; and/or an arginine (R) corresponding to the 265th amino acid of SEQ ID NO:2. In some embodiments, the polypeptide is depicted in SEQ ID NO:2. In some embodiments, the polynucleotide comprises SEQ ID NO:1.

DEFINITIONS

"Alkaline phosphatase activity" refers to the enzymatic activity for removing 5' phosphate groups from nucleic acids.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein). A polynucleotide sequence is "heterologous to" an organism if it originates from a foreign species, or, if from the same species, is modified from its original form, i.e. it is not linked to flanking chromosomal DNA exactly as it is found in the species from which the sequence is derived.

The phrase "a nucleic acid sequence encoding" refers to a nucleic acid which contains sequence information for a structural RNA such as rRNA, a tRNA, or the primary amino acid sequence of a specific protein or peptide, or a binding site for a transacting regulatory agent. This phrase specifically encompasses degenerate codons (i.e., different codons which encode a single amino acid) of the native sequence or sequences that may be introduced to conform with codon preference in a specific host cell.

An amino acid of a first protein "corresponding" to a position in a reference protein refers to the amino acid in the first protein is aligned with the position in the reference protein when the first protein and reference protein sequences are aligned. Alignment of sequences can be performed with standard software, including the BLAST algorithm, as described below.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "nucleic acid" or "polynucleotide" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); and Cassol et al. (1992); Rossolini et al., *Mol. Cell. Probes* 8:91–98 (1994)). The term nucleic acid is used interchangeably with gene, cDNA, and mRNA encoded by a gene.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full length proteins (i.e., antigens), wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As for amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:

1) Alanine (A), Glycine (G);

2) Aspartic acid (D), Glutamic acid (E);

3) Asparagine (N), Glutamine (Q);

4) Arginine (R), Lysine (K);

5) Isoleucine (I), Leucine (L), Methionine (M), Valine (V);

6) Phenylalanine (F), Tyrosine (Y), Tryptophan (W);

7) Serine (S), Threonine (T); and

8) Cysteine (C), Methionine (M)

(see, e.g., Creighton, *Proteins* (1984)).

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, 95%, 97%, 98% or 99% identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length.

The term "similarity," or percent "similarity," in the context of two or more polypeptide sequences, refer to two or more sequences or subsequences that have a specified percentage of amino acid residues that are either the same or similar as defined in the 8 conservative amino acid substitutions defined above (i.e., 60%, optionally 65%, 70%, 75%, 80%, 85%, 90%, or 95% similar over a specified region or the entire sequence of a polynucleotide, e.g., encoding rat SEAP (e.g., SEQ ID NO:2), when compared and aligned for maximum correspondence over a comparison window, or designated region as measured using one of the following sequence comparison algorithms or by manual alignment and visual inspection. Such sequences are then said to be "substantially similar." Optionally, this identity exists over a region that is at least about 50 amino acids in length, or more preferably over a region that is at least about 100 to 500 or 1000 or more amino acids in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (1977) *Nuc. Acids Res.* 25:3389–3402, and Altschul et al. (1990) *J. Mol. Biol.* 215:403–410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873–5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The BLAST algorithm can be used to determine whether an amino acid in a polypeptide "corresponds to" an amino acid in SEQ ID NO:2. If BLAST aligns two polypeptide sequences and an amino acid in one sequence is identical to the amino acid aligned in the second sequence, then the amino acids correspond.

BRIEF DESCRIPTION OF THE DRAWINGS

Figure 2:
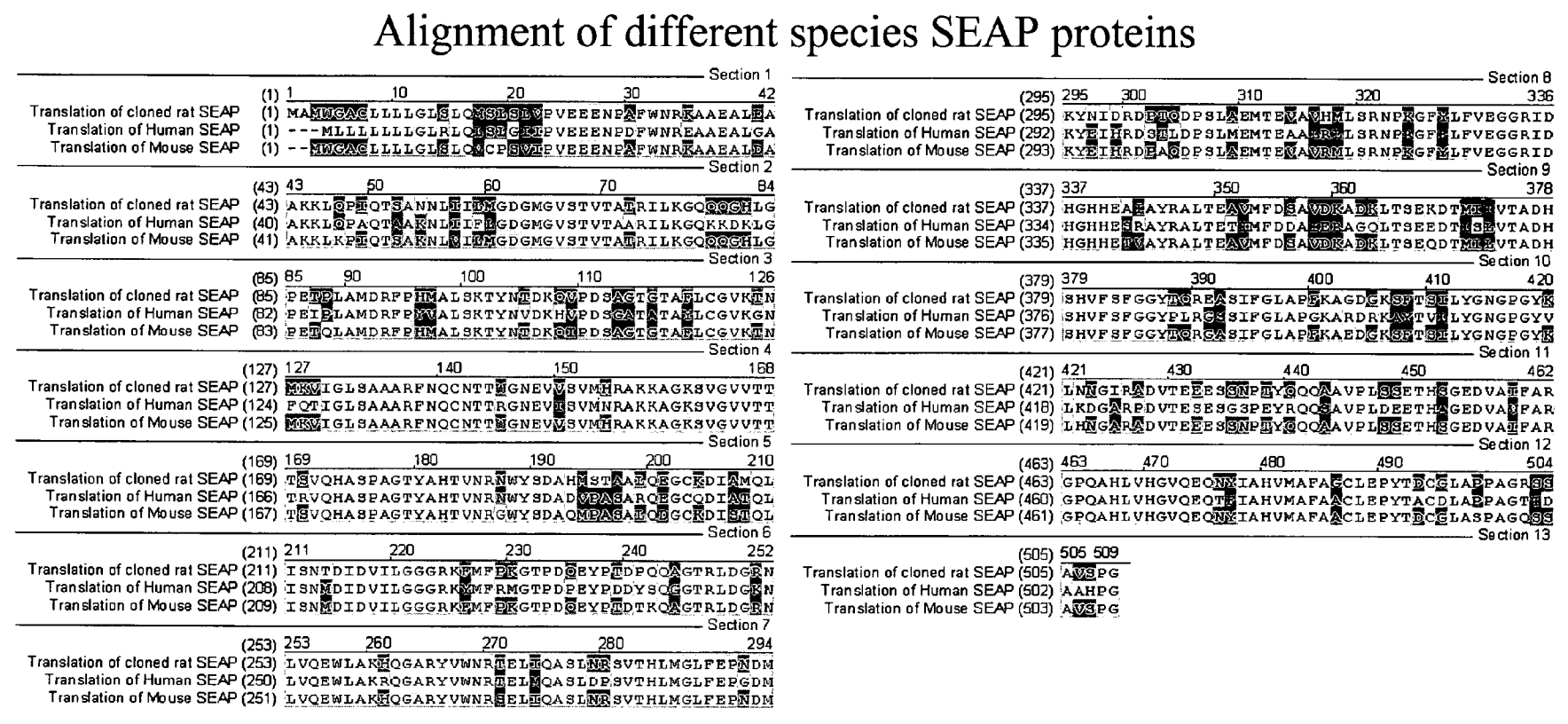

FIG. 2 presents an alignment of the amino acid sequences of human (SEQ ID NO:2), mouse (SEQ ID NO:3) and rat (SEQ ID NO:4) SEAP proteins.

DETAILED DESCRIPTION OF THE INVENTION

I. Introduction

Figure 1:
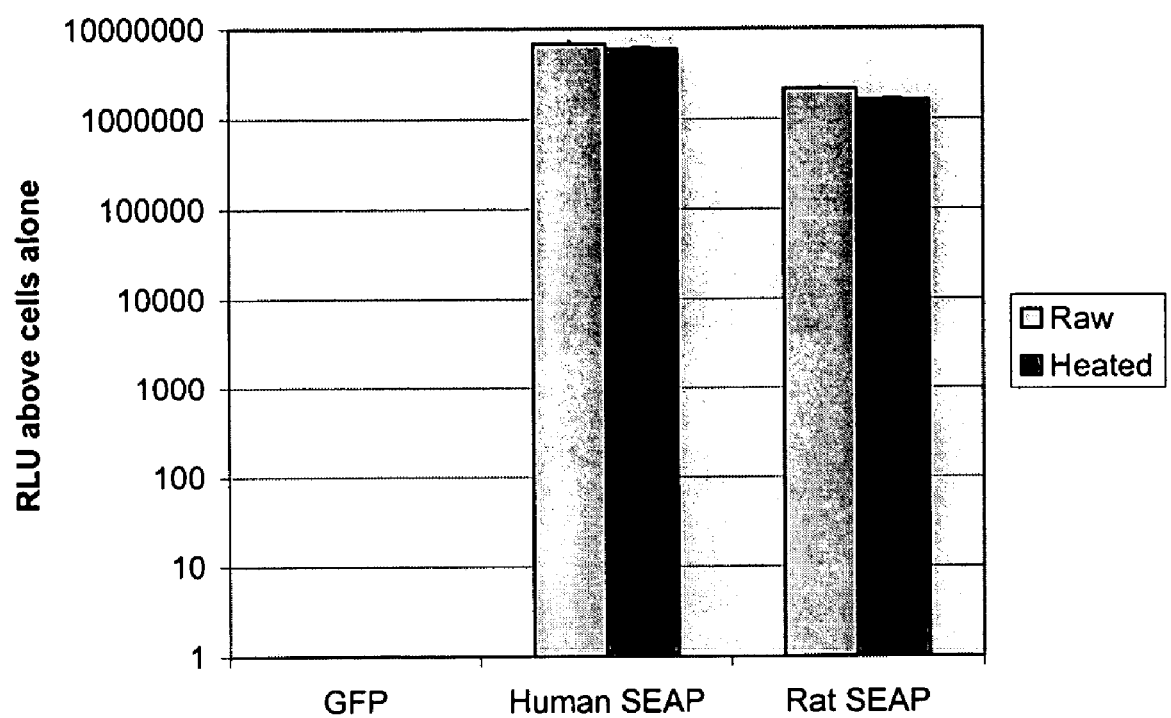
FIG. 1 illustrates that rat SEAP shows heat-stable alkaline phosphatase in standard alkaline phosphatase assay.

The present invention is based in part on the identification and cloning of the rat embryonic alkaline phosphatase (rSEAP) and creation of the secreted form of the enzyme. The cloning of rSEAP will be used to address one of the biggest hurdles in gene therapy, i.e., long term expression of transgenes. For example, current investigations of loss of adenoviral expression are complicated by the presence of reporter transgenes that are immunogenic. This invention will facilitate evaluation and development of gene transfer vectors, including both viral and non-viral vectors, for gene therapy, target validation and other applications. The rSEAP sequence is particularly useful in rats where it has low or no immunogenic properties, is secreted for easy detection and has low background. Secreted proteins provide a non-invasive detection for prolonged studies of expression. Rat SEAP can also be used as a readily quantifiable reporter in other systems where a quantitative measurement is desired.

Rats are useful host animals for experimentation because they provide a larger animal model where frequent blood sampling could occur without risk to the animal compared to mice. Several benefits of the present invention include highly sensitive assays and a modified enzyme that is secreted rather than membrane bound. Secretion of the enzyme reduces the background from endogenous phosphatases. The rat SEAP is also thermostable at 65° C. and resistant to inhibitors such as L-homoarginine and levamisole. Finally, highly sensitive assays have been developed which offer a broad range of linearity to quantify alkaline phosphatase activity. See, Bronstein, et al. *Biotechniques* 17:172–4, 176–7 (1994); Bronstein, et al. *Clin Chem* 42:1542–6 (1996).

The cloned rat secreted alkaline phosphatase gene described in this invention can be, e.g., cloned into a series of adenovirus vectors where it is used to look at modifications in the adenovirus backbone which alter the immunogenic nature of the virally-expressed environment. In addition, this reporter construct can be used in the development of rat models, in particular tumor models, and other applications for a non-immunogenic reporter in rats.

II. General Recombinant Nucleic Acid Methods for Use with the Invention

In numerous embodiments of the present invention, nucleic acids encoding a rSEAP will be isolated and cloned using recombinant methods. Such embodiments are used, e.g., to isolate rSEAP polynucleotides (e.g., SEQ ID NO:1) for protein expression or during the generation of variants, derivatives, expression cassettes, or other sequences derived from an rSEAP polypeptide (e.g., SEQ ID NO:2), to monitor rSEAP gene expression, for diagnostic purposes in a patient, or to detect expression levels of rSEAP nucleic acids or rSEAP polypeptides. In some embodiments, the sequences encoding the rSEAP of the invention are operably linked to a heterologous promoter.

In some embodiments, rSEAP polynucleotides encode rSEAP polypeptides at least about 70%, 80%, 90%, 92%, 93%, 95%, 98% or 99% identical to SEQ ID NO:2. In some embodiments, the rSEAP polypeptide described above comprise a methionine (M) corresponding to the first amino acid of SEQ ID NO:2; an alanine (A) corresponding to the second amino acid of SEQ ID NO:2; and/or an arginine (R) corresponding to the 265th amino acid of SEQ ID NO:2. In some embodiments, the rSEAP polynucleotides of the invention do not include those set forth in Genbank accession number XM_237353 or XM_237355.

One benefit of the rSEAP is its use to monitor gene expression in an mammal, for example in gene therapy, for long periods of time. In some embodiments, the mammal in which rSEAP is expressed is rat, though the protein can also be expressed in other mammals including mice, primates, etc. In some embodiments, rSEAP activity is measured in the mammal at least 10, 20, 30, 40, 50, 90 or more days after administration of a vector encoding rSEAP.

This invention relies on routine techniques in the field of recombinant genetics. Basic texts disclosing the general methods of use in this invention include Sambrook et al., *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

In general, the nucleic acids encoding the subject proteins are cloned from DNA sequence libraries that are made to encode cDNA or genomic DNA. The particular sequences can be located by hybridizing with an oligonucleotide probe, the sequence of which can be derived from SEQ ID NO:1 or encoding SEQ ID NO:2, which provides a reference for PCR primers and defines suitable regions for isolating rSEAP specific probes. Alternatively, where the sequence is cloned into an expression library, the expressed recombinant protein can be detected immunologically with antisera or purified antibodies made against the rSEAP of interest.

III. Vectors

The present invention provides expression cassettes and vectors comprising polynucleotides encoding rSEAP polypeptides of the invention. In many embodiments, a promoter is operably linked to a polynucleotide encoding rSEAP of the invention. In some cases, the promoter is inducible or tissue-specific. Exemplary tissue-specific promoters include those specific for the bladder, e.g., the uroplakin2 promoter. See e.g., Zhu et al., *Urol Res.* 31(1): 17–21 (2003); Zhang et al., Cancer Res. 62(13):3743–50 (2002).

The invention provides for any nucleic acid or nucleic acid-bearing particle or composition, cell, or organism capable of being used to transfer a nucleic acid into a host cell. Vectors can be viral or non-viral and can be used in vitro, ex vivo, or in vivo. Non-viral vectors include, e.g., plasmids, cosmids, and can comprise liposomes, electrically charged lipids (cytofectins), DNA-protein complexes, and biopolymers. Viral vectors include, e.g., retroviruses, lentiviruses, adeno-associated virus, pox viruses, baculovirus, reoviruses, vaccinia viruses, herpes simplex viruses, Epstein-Barr viruses, and adenovirus vectors.

IV. Host Cells and Animals rSEAP can be expressed in any prokaryotic or eukaryotic cell. Similarly, rSEAP can be expressed in any animal. As discussed above, in some embodiment rSEAP is expressed in a rat or other animal that does not react immunologically with rSEAP. rSEAP can be expressed in, e.g., humans, mice, dogs, cats, primates, bovine, horse, pigs, etc. Expression cassettes and vectors can be introduced into cells and animals by any methods known to those in the art. Cells recombinantly-expressing rSEAP can be normal or tumor cells. In one application of the invention, tumor cells are transformed to express rSEAP and can then be used to screen for tumor inhibitors using rSEAP as a reporter. Similarly, cells transformed with an expression cassette in which a polynucleotide encoding rSEAP is operably-linked to a tumor-specific promoter can be used to monitor tumor cells in a mixture of cell.

Conventional viral and non-viral based gene transfer methods can be used to introduce nucleic acids encoding engineered polypeptides of the invention in mammalian cells or target tissues. Such methods can be used to administer nucleic acids encoding polypeptides of the invention to cells in vitro. In some embodiments, the nucleic acids encoding polypeptides of the invention are administered for in vivo or ex vivo gene therapy uses. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. For a review of gene therapy procedures, see Anderson, *Science* 256:808–813 (1992); Nabel & Felgner, *TIBTECH* 11:211–217 (1993); Mitani & Caskey, *TIBTECH* 11:162–166 (1993); Dillon, *TIBTECH* 11:167–175 (1993); Miller, *Nature* 357:455–460 (1992); Van Brunt, *Biotechnology* 6(10):1149–1154 (1988); Vigne, *Restorative Neurology and Neuroscience* 8:35–36 (1995); Kremer & Perricaudet, *British Medical Bulletin* 51(1):31–44 (1995); Haddada et al., in *Current Topics in Microbiology and Immunology* Doerfler and Böhm (eds) (1995); and Yu et al., *Gene Therapy* 1:13–26 (1994).

Methods of non-viral delivery of nucleic acids encoding engineered polypeptides of the invention include lipofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404–410 (1995); Blaese et al., *Cancer Gene Ther.* 2:291–297 (1995); Behr et al., *Bioconjugate Chem.* 5:382–389 (1994); Remy et al., *Bioconjugate Chem.* 5:647–654 (1994); Gao et al., *Gene Therapy* 2:710–722 (1995); Ahmad et al., *Cancer Res.* 52:4817–4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids encoding engineered polypeptides of the invention take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo) Conventional viral based systems for the delivery of polypeptides of the invention could include retroviral, lentivirus, adenoviral, adeno-associated and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6–10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., *J. Virol.* 66:2731–2739 (1992); Johann et al., *J. Virol.* 66:1635–1640 (1992); Sommerfelt et al., *Virol.* 176:58–59 (1990); Wilson et al., *J. Virol.* 63:2374–2378 (1989); Miller et al., *J. Virol.* 65:2220–2224 (1991); PCT/US94/05700).

Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:3847 (1987); U.S. Pat. No. 4,797,368; WO 93/24641; Kotin, *Human Gene Therapy* 5:793–801 (1994); Muzyczka, *J. Clin. Invest.* 94:1351 (1994)). Construction of recombinant AAV vectors is described in a number of publications, including U.S. Pat. No. 5,173,414; Tratschin et al., *Mol. Cell. Biol.* 5:3251–3260 (1985); Tratschin, et al., *Mol. Cell. Biol.* 4:2072–2081 (1984); Hermonat & Muzyczka, *PNAS* 81:6466–6470 (1984); and Samulski et al., *J. Virol.* 63:03822–3828 (1989).

pLASN and MFG-S are examples are retroviral vectors that have been used in clinical trials (Dunbar et al., *Blood* 85:3048–305 (1995); Kohn et al., *Nat. Med.* 1:1017–102 (1995); Malech et al., *PNAS* 94:22 12133–12138 (1997)). PA317/pLASN was the first therapeutic vector used in a gene therapy trial. (Blaese et al., *Science* 270:475–480 (1995)). Transduction efficiencies of 50% or greater have been observed for MFG-S packaged vectors. (Ellem et al., *Immunol Immunother.* 44(1):10–20 (1997); Dranoff et al., *Hum. Gene Ther.* 1:111–2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702–3 (1998), Kearns et al., *Gene Ther.* 9:748–55 (1996)).

Replication-deficient recombinant adenoviral vectors (Ad) can be engineered such that a transgene replaces the Ad E1a, E1b, and E3 genes; subsequently the replication defector vector is propagated in human 293 cells that supply deleted gene function in trans. Ad vectors can transduce multiply types of tissues in vivo, including nondividing, differentiated cells such as those found in the liver, kidney and muscle system tissues. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083–9 (1998)). Additional examples of the use of adenovirus vectors for gene transfer in clinical trials include Rosenecker et al., *Infection* 24:1 5–10 (1996); Sterman et al., *Hum. Gene Ther.* 9:7 1083–1089 (1998); Welsh et al., *Hum. Gene Ther.* 2:205–18 (1995); Alvarez et al., *Hum. Gene Ther.* 5:597–613 (1997); Topf et al., *Gene Ther.* 5:507–513 (1998); Sterman et al., *Hum. Gene Ther.* 7:1083–1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by producer cell line that packages a nucleic acid vector into a viral particle. The vectors typically contain the minimal viral sequences required for packaging and subsequent integration into a host, other viral sequences being replaced by an expression cassette for the protein to be expressed. The missing viral functions are supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. A viral vector is typically modified to have specificity for a given cell type by expressing a ligand as a fusion protein with a viral coat protein on the viruses outer surface. The ligand is chosen to have affinity for a receptor known to be present on the cell type of interest. For example, Han et al., *PNAS* 92:9747–9751 (1995), reported that Moloney murine leukemia virus can be modified to express human heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g., Fab or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In some embodiments, cells are isolated from the subject organism, transfected with a nucleic acid (gene or cDNA) encoding a polypeptides of the invention, and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-γ and TNF-α are known (see Inaba et al., *J. Exp. Med.* 176:1693–1702 (1992)).

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+ (panB cells), GR-1 (granulocytes), and Iad (differentiated antigen presenting cells) (see Inaba et al., *J. Exp. Med.* 176:1693–1702 (1992)).

Vectors (e.g., retroviruses, adenoviruses, liposomes, etc.) containing therapeutic nucleic acids can be also administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

Pharmaceutically acceptable carriers or excipients are determined in part by the particular composition being administered, as well as by the particular method used to administer the composition. Accordingly, there is a wide variety of suitable formulations of pharmaceutical compositions of the present invention, as described below (see, e.g., *Remington's Pharmaceutical Sciences*, 17th ed., 1989). An exemplary excipient is SYN3. See, e.g., PCT/US02/41198.

VI. Detecting rSEAP rSEAP can be detected in an animal or cell culture by any means. For example, the presence of the protein can be detected by detecting alkaline phosphatase activity (e.g., using StarBright® Green Substrate from Sigma Aldrich) or rSEAP protein levels in blood or serum from an animal or in cell culture media when measured in cell cultures.

Alternatively, any sort of appropriate immunological detection including, e.g., ELISA assays, western blotting or immunohistochemical detection can be used. Immunoassays can be used to qualitatively or quantitatively analyze rSEAP. A general overview of the applicable technology can be found in Harlow & Lane, *Antibodies: A Laboratory Manual* (1988).

EXAMPLES

A search of Genbank and the Rat Genome Project databases was performed using both the mouse cDNA and genomic sequences as bait. Only two hits where found from Genbank (AC128893 and AC114387) which are unordered fragments from the human genome project. By aligning both mouse and human with the sequences obtained from the database a theoretical cDNA for the rat SEAP was created. Using this sequence, a series of 5 primers were designed; one to prime cDNA synthesis from the RNA target (RSEP-R3), a pair to amplify the complete cDNA (RSEP-F2 and RSEP-R2) and a final pair to amplify the coding region and remove the last 20 amino acids of the protein (RSEP-F and RSEP-R).

Reverse transcription of total rat embryo RNA (Ambion, Inc. Cat #7928) with RSEP-R3 as the primer was performed followed by two rounds of PCR using each set of primers described above. The final product was gel purified and digested with SalI and NotI to liberate the coding region. The DNA fragment was then cloned into pTV327-polyA-GFP-CMV after excising of the GFP gene. Sequencing of resulting pTV327-Rat SEAP clones was used to identify those containing the wild-type cDNA. Alignment of the new sequence showed high homology to the mouse and human cDNAs. At the amino acid level the rat shares 92% homology to mouse and 76% to human.

To demonstrate biological activity of the new gene, 293 cells were transfected with the pTV327-Rat SEAP DNA and assayed for activity 48 hours latter. The media was assayed with the Phospha-Light™ Secreted Alkaline Phosphatase Reporter Gene Assay System from Applied Biosystems. FIG. 1 shows a strong signal obtained from the 293 cells transfected with the rat SEAP gene The above example is provided to illustrate the invention but not to limit its scope. Other variants of the invention will be readily apparent to one of ordinary skill in the art and are encompassed by the appended claims. All publications, databases, Genbank sequences, patents, and patent applications cited herein are hereby incorporated by reference.

What is claimed is:

1. An isolated polynucleotide encoding a polypeptide at least 95% identical to SEQ ID NO:2, wherein the polypeptide has alkaline phosphatase activity.

2. The isolated polynucleotide of claim 1, wherein the polypeptide comprises
a methionine (M) corresponding to the first amino acid of SEQ ID NO:2.

3. The isolated polynucleotide of claim 1, wherein the polypeptide is depicted in SEQ ID NO:2.

4. The isolated polynucleotide of claim 1, wherein the polynucleotide comprises SEQ ID NO:1.

5. An expression cassette comprising a promoter operably linked to a polynucleotide encoding a polypeptide at least 95% identical to SEQ ID NO:2, wherein the polypeptide has alkaline phosphatase activity.

6. The expression cassette of claim 5, wherein the promoter is constitutive.

7. The expression cassette of claim 5, wherein the promoter is inducible.

8. The expression cassette of claim 5, wherein the promoter is tissue-specific.

9. A vector comprising a promoter operably-linked to a polynucleotide encoding a polypeptide at least 95% identical to SEQ ID NO:2, wherein the polypeptide has alkaline phosphatase activity.

10. The vector of claim 9, wherein the polypeptide comprises
a methionine (M) corresponding to the first amino acid of SEQ ID NO:2.

11. The vector of claim 9, wherein the polypeptide comprises SEQ ID NO:2.

12. The vector of claim 9, wherein the polynucleotide comprises SEQ ID NO:1.

13. The vector of claim 9, wherein the vector is a viral vector.

14. The vector of claim 9, wherein the vector is an adenoviral vector.

15. The vector of claim 9, wherein the vector comprises a second expression cassette encoding a second polypeptide.

16. The vector of claim 9, wherein the vector is a plasmid.

17. An isolated cell comprising a heterologous expression cassette, wherein the expression cassette comprises a promoter operably linked to a polynucleotide encoding a polypeptide at least 95% identical to SEQ ID NO:2, and wherein the polypeptide has alkaline phosphatase activity.

18. The cell of claim 17, wherein the polypeptide comprises
a methionine (M) corresponding to the first amino acid of SEQ ID NO:2.

19. The cell of claim 17, wherein the polypeptide comprises SEQ ID NO:2.

20. The cell of claim 17, wherein the polynucleotide comprises SEQ ID NO:1.

21. The cell of claim 17, wherein the expression cassette is integrated into the chromosomal DNA of the cell.

22. The cell of claim 17, wherein the expression cassette is part of a vector.

23. The cell of claim 17, wherein the vector is a viral vector.

24. The cell of claim 17, wherein the vector is an adenoviral vector.

25. The cell of claim 17, wherein the cell is a mammalian cell.

26. The cell of claim 17, wherein the cell is a rat cell.

27. The cell of claim 17, wherein the cell is a prokaryotic cell.

28. A method of expressing secreted embryonic alkaline phosphatase in an isolated cell, the method comprising introducing into the cell a nucleic acid comprising an expression cassette comprised of a promoter operably linked to a polynucleotide encoding a polypeptide at least 95% identical to SEQ ID NO: 2, wherein the polypeptide has alkaline phosphatase activity, culturing the cell and thereby expressing secreted embryonic alkaline phosphatase in the cell.

29. The method of claim 28, wherein the polypeptide comprises
a methionine (M) corresponding to the first amino acid of SEQ ID NO:2.

30. The method of claim 28, wherein the polypeptide comprises SEQ ID NO:2.

31. The method of claim 28, wherein the polynucleotide comprises SEQ ID NO:1.

32. The method of claim 28, wherein the nucleic acid is a viral vector.

33. The method of claim 28, wherein the viral vector is an adenoviral vector.

34. The method of claim 28, wherein the viral vector comprises a second expression cassette encoding a second polypeptide.

35. The isolated polynucleotide of claim 1, wherein the polypeptide comprises an alanine (A) corresponding to the second amino acid of SEQ ID NO:2.

36. The isolated polynucleotide of claim 1, wherein the polypeptide comprises an arginine (R) corresponding to the 265th amino acid of SEQ ID NO:2.

37. The vector of claim 9, wherein the polypeptide comprises an alanine (A) corresponding to the second amino acid of SEQ ID NO:2.

38. The vector of claim 9, wherein the polypeptide comprises an arginine (R) corresponding to the 265th amino acid of SEQ ID NO:2.

39. The cell of claim 17, wherein the polypeptide comprises an alanine (A) corresponding to the second amino acid of SEQ ID NO:2.

40. The cell of claim 17, wherein the polypeptide comprises an arginine (R) corresponding to the 265th amino acid of SEQ ID NO:2.

41. The method of claim 28, wherein the polypeptide comprises an alanine (A) corresponding to the second amino acid of SEQ ID NO:2.

42. The method of claim 28, wherein the polypeptide comprises an arginine (R) corresponding to the 265th amino acid of SEQ ID NO:2.

* * * * *